United States Patent
DeCrescenzo et al.

(10) Patent No.: US 8,303,619 B2
(45) Date of Patent: Nov. 6, 2012

(54) NOSEBLEED TREATMENT APPARATUS AND ASSOCIATED METHOD

(76) Inventors: Anne DeCrescenzo, Sewaren, NJ (US); Dominick DeCrescenzo, Sewaren, NJ (US)

( * ) Notice: Subject to any disclaimer, the term of this patent is extended or adjusted under 35 U.S.C. 154(b) by 632 days.

(21) Appl. No.: 12/454,289

(22) Filed: May 15, 2009

(65) Prior Publication Data
US 2009/0299405 A1 Dec. 3, 2009

Related U.S. Application Data

(60) Provisional application No. 61/128,872, filed on May 27, 2008.

(51) Int. Cl.
*A61B 17/00* (2006.01)
(52) U.S. Cl. .... 606/201; 606/196; 606/199; 606/204.45
(58) Field of Classification Search .................. 606/196, 606/199, 201, 204.45; 381/71.6, 309, 370, 381/376
See application file for complete search history.

(56) References Cited

U.S. PATENT DOCUMENTS

| | | | |
|---|---|---|---|
| 3,349,771 A | 10/1967 | Bear | |
| 4,820,266 A | 4/1989 | Berry | |
| 5,885,675 A * | 3/1999 | Martin | 428/36.5 |
| 5,899,918 A * | 5/1999 | Knott et al. | 606/204 |

* cited by examiner

*Primary Examiner* — Gary Jackson
*Assistant Examiner* — Kevin Everage

(57) ABSTRACT

The nosebleed treatment apparatus features a pair of pliable mirror image nose pads comprising a first nose pad and a second nose pad. A gel pack is disposed within each nose pad. Each gel pack has a first side spaced apart from a second side. The first side is adjacent to an inner surface of the medial pad section. The second side is disposed within the lateral pad section. A smooth shouldered reinforcement member is disposed atop each nose pad. A U-shaped oblong tensing member connects the first nose pad to the second nose pad at each reinforcement member. The apparatus can be placed in a freezer or cooler for extended cool retention within the gel packs when removed. Upon removal, the apparatus is placed on a bleeding nose and remains until removed, so that a patient need not hold it in place.

16 Claims, 10 Drawing Sheets

NOSEBLEED TREATMENT APPARATUS AND ASSOCIATED METHOD

CROSS REFERENCE TO RELATED APPLICATIONS

This application claims the benefit of U.S. Provisional Application No. 61/128,872 filed May 27, 2008 the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to first aid devices and, more particularly, to a thermally-activated first aid device for effectively halting nosebleeds.

2. Prior Art

Nosebleeds, or epistaxis, are episodes of profuse bleeding from within the nose. Twice as common in children as in adults, nosebleeds are usually more frightening than genuinely hazardous, although they can also be symptomatic of very serious conditions including high blood pressure, cancer, blood clotting disorders, and cocaine abuse.

In children, nosebleeds tend to occur from within the front of the nose, while adults may experience a more severe bleeding from high up within the nasal passages or sinus cavities. Nosebleeds, generally, can be stopped by continuous application, for five minutes or so, of pressure to both sides of the nose, preferably combined with cold, such as an ice bag or cold-pack.

Medical experts advise that, if the bleeding has not stopped after two such periods of pressure, the patient should seek medical care immediately. For the person suffering a nosebleed, the experience is unsettling and alarming, and presents an immediate and practical problem: with one hand they are supposed to hold the two sides of the nose tightly closed, somehow applying an ice pack at the same time, and with the other they are supposed to hold a cloth, handkerchief, paper towels, or other absorbent material to their nose, which is still bleeding copiously. This is virtually impossible, and can lead the sufferer to experience not only the nosebleed, but symptoms of a panic attack as well.

Accordingly, the present invention is disclosed in order to overcome the above noted problems. The first aid device is convenient and easy to use, lightweight yet durable in design, and designed for many years of repeated use.

SUMMARY OF THE INVENTION

In view of the foregoing background, it is therefore an object of the present invention to provide an apparatus for a nosebleed treatment apparatus. These and other objects, features, and advantages of the invention are provided by a apparatus that may be applied to the nose of the patient and thereafter remain clamped there, the patient's hands may be free for the other task—that of holding up tissues, cloths, or paper towels to stanch and contain the flow of blood.

The apparatus may not only apply pressure to either side of the patient's nose, but may apply a cold-pack as well—thus fulfilling the two prescribed modes of treatment recommended for nosebleeds by authorities on first-aid. The pressure on the nose is essential to stopping blood flow, while the cold-packs not only assist in stopping the flow, but also work to reduce the consequential inflammation and swelling that may otherwise occur.

Compact and easy to use, the apparatus may replace the awkward measures that nosebleed sufferers have been saddled with in the past. With this first aid apparatus, the sufferer may simply remove the apparatus from the freezer, apply it to the nose, and continue to stanch the flow of blood with appropriate catchments materials until the apparatus has stopped the bleeding.

In one embodiment, the first aid apparatus may be a small padded clamp designed to fit snugly on the bridge of the patient's nose, and may apply both continuous pressure and the cooling effects of a cold pack. The first aid apparatus may resemble an inverted "U" in shape, and may measure 1 to 1½" in height, for example, with various widths to accommodate variously sized noses.

The two nose-pads of the apparatus may provide two firm but smoothly padded pressure points on opposite sides of the nose. These pads may also be gel "cold-packs," composed of a gel material that can be stored in the freezer for use, and will stay cold for long periods when removed from the freezer. The inverted "U" shape of the first aid apparatus is actually a tensing member that stores elastic energy as it is forced open and placed on the nose, where it converts the elastic energy to kinetic energy, forcing the nose closed and thus promoting an end to the bleeding.

The cold pack pads, by lowering the temperature of the affected area, also promote clotting, and decrease the inflammation and swelling of tissues. The first aid apparatus could be manufactured in a variety of colors and styles, perhaps incorporating fanciful themes, colors, or designs for children, reassuring them at a time of fear; and in a variety of sizes and colors for adults.

The apparatus could be sold as an individual unit, or in a handy family pack; but in each case, the first aid apparatus is designed for multiple uses, and would require nothing more than a good washing between uses. The apparatus could be stored in the freezer between uses, thereby keeping the cold pack nose-pads cold and read for use.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

Figure 1:
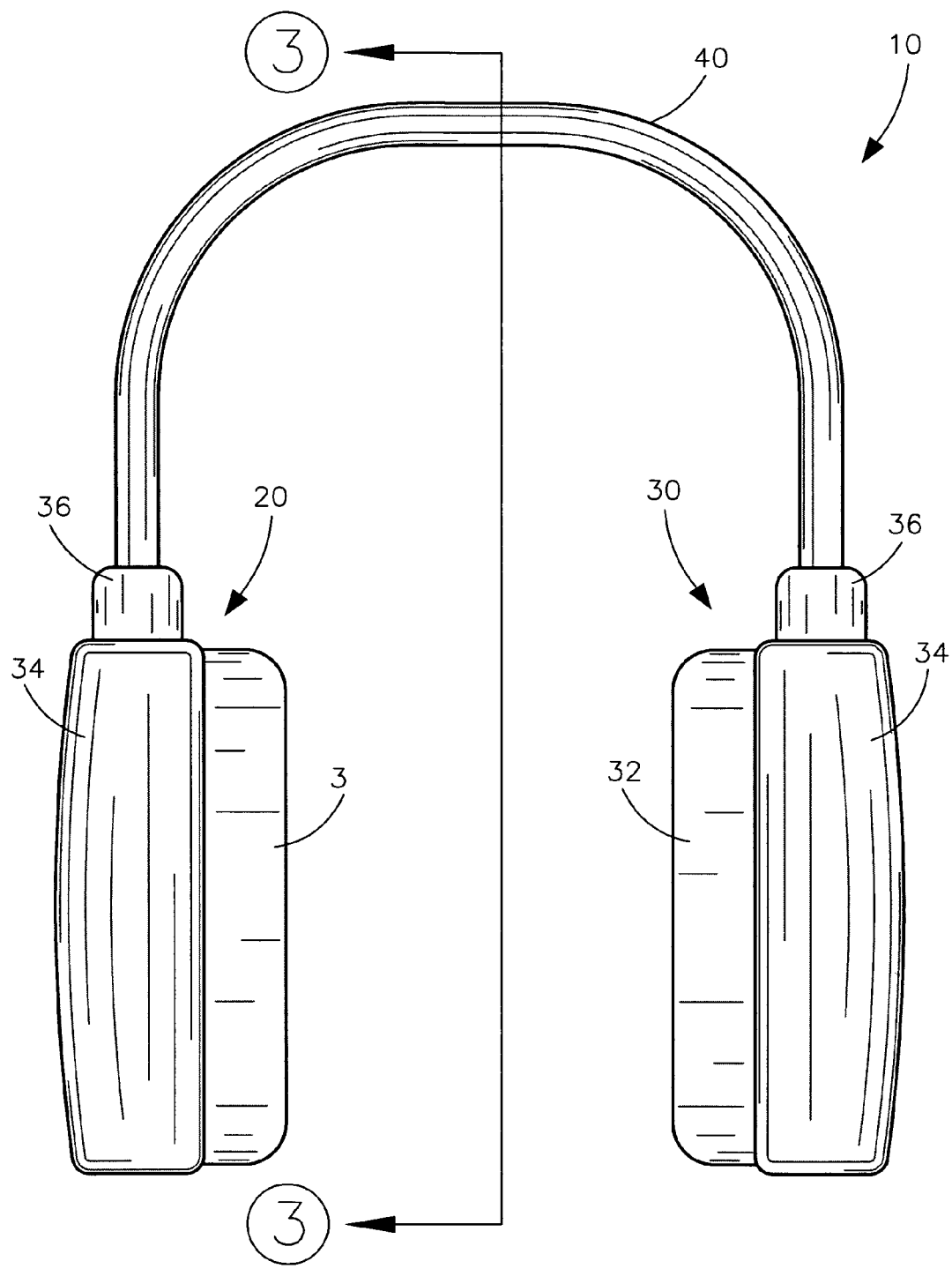
FIG. 1 is a front elevation view showing the nosebleed treatment apparatus, in accordance with one embodiment of the present invention.

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The apparatus of this invention is referred to generally in FIGS. 1-10b by the reference numeral 10 and is intended to provide a nosebleed treatment apparatus 10. It should be understood that the nosebleed treatment apparatus 10 may be used to halt a nosebleed and reduce swelling with many different types of other useful applications. For example, the apparatus 10 can be used on fingers and toes to reduce and control swelling.

Referring to FIG. 1, the nosebleed treatment apparatus 10 preferably includes a pair of pliable mirror image nose pads including a first nose pad 20 and a second nose pad 30. Each nose pad 20, 30 has a medial pad section 32 melded into a larger lateral pad section 34. Each pad section 20, 30 may have a generally rectangular shape.

Figure 4:
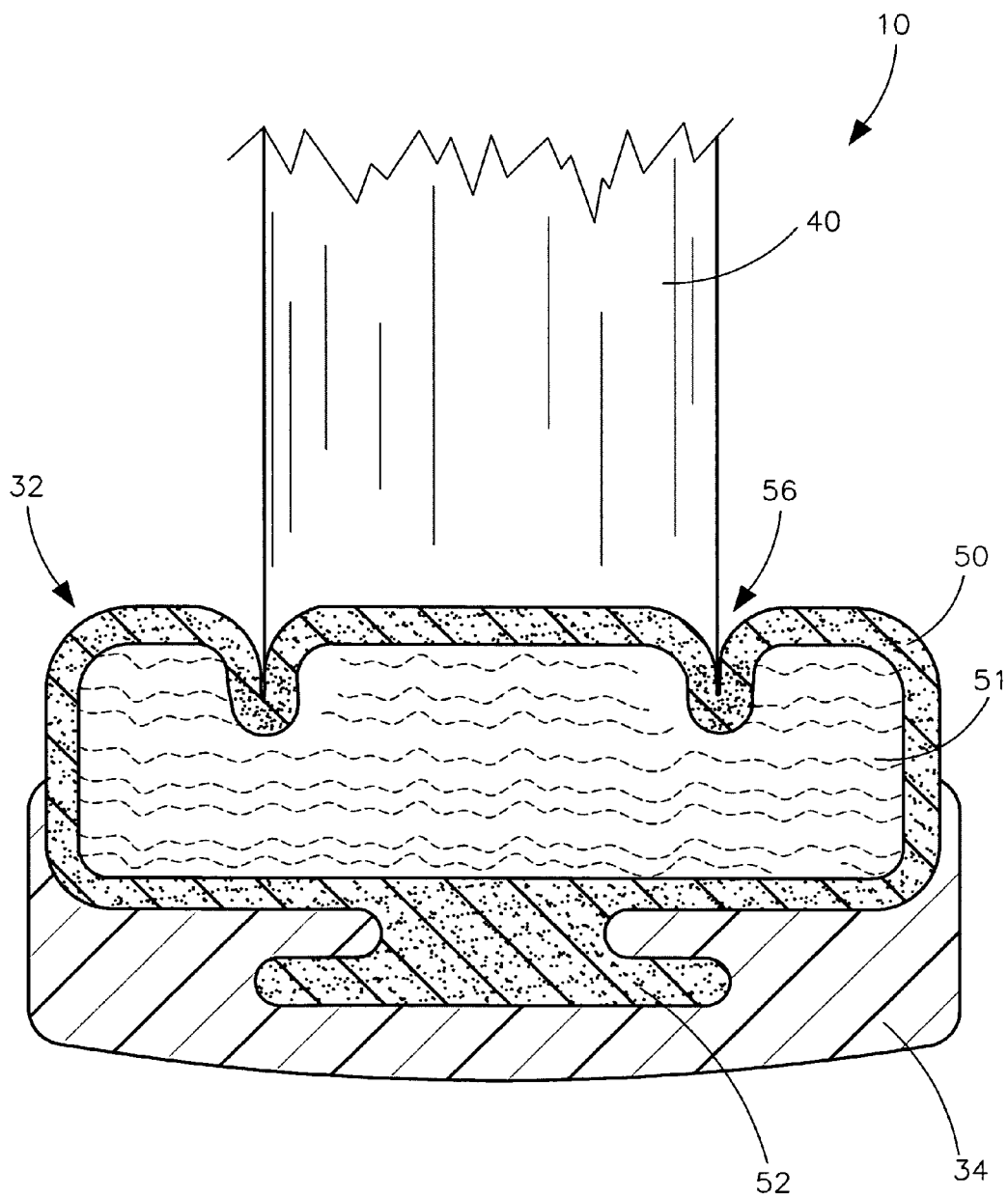
FIG. 4 is cross sectional view of FIG. 3, taken along the line 4-4, showing the gel pack design within the first pad, a mirror image of the second pad.
Figure 5:
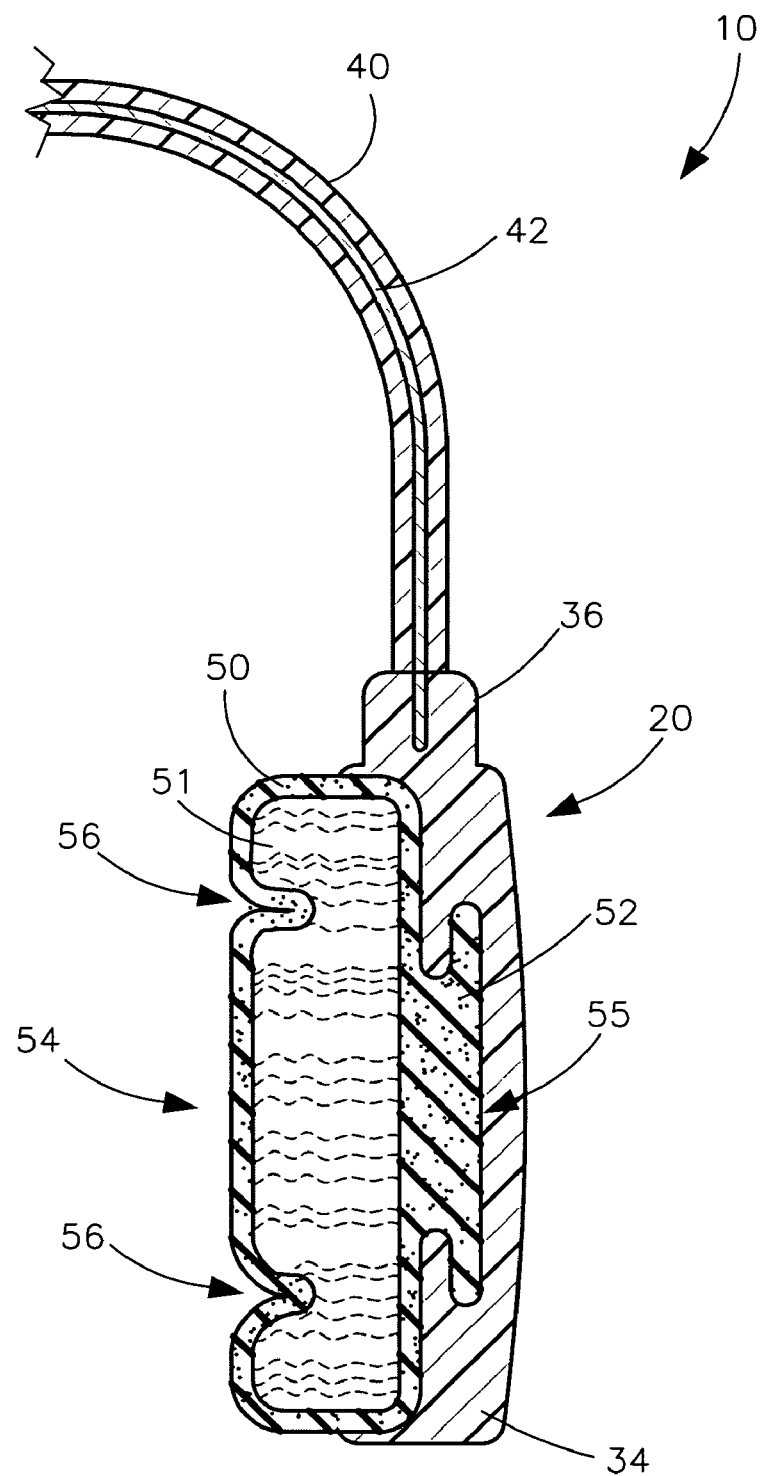
FIG. 5 is cross sectional view of FIG. 3, taken along the line 5-5, showing the gel pack within the pad, the reinforcement member of the gel pack statically connected to the tension member, and the memory wire statically situated within the tensing member, in accordance with one embodiment of the present invention.

Referring to FIGS. 4 and 5, each pad 20, 30 further includes a gel pack 50 filled with gel 51 disposed within each nose pad 20, 30. Each gel pack 50 has a first side 54 spaced apart from a second side 55. The first side 54 is adjacent to the inner surface 59 of the medial pad section 32. The second side 55 has a flared bolster 52 disposed within the lateral pad section 34. The bolster importantly adds to the structural integrity of the nose pads 20, 30 and their containment of the gel packs 50.

Figure 3:
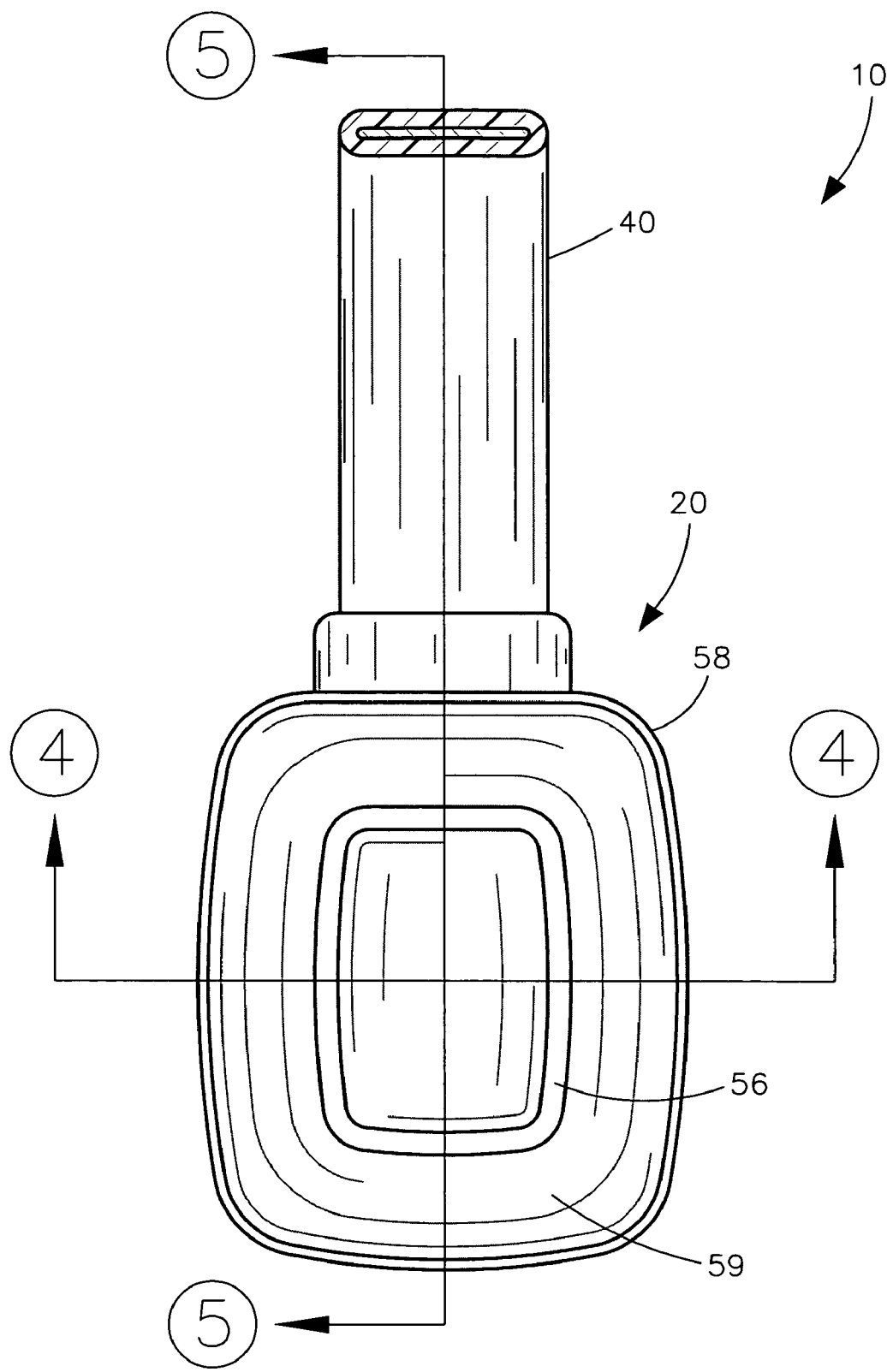
FIG. 3 is a cross sectional view of FIG. a, taken along the line 3-3, showing the first pad and a part of the tensing member.

Referring still to FIGS. 4 and 5 and referring also to FIG. 3, a rectangular depression 56 is spaced inwardly from the outer border 58 of the medial pad section 32.

Figure 2:
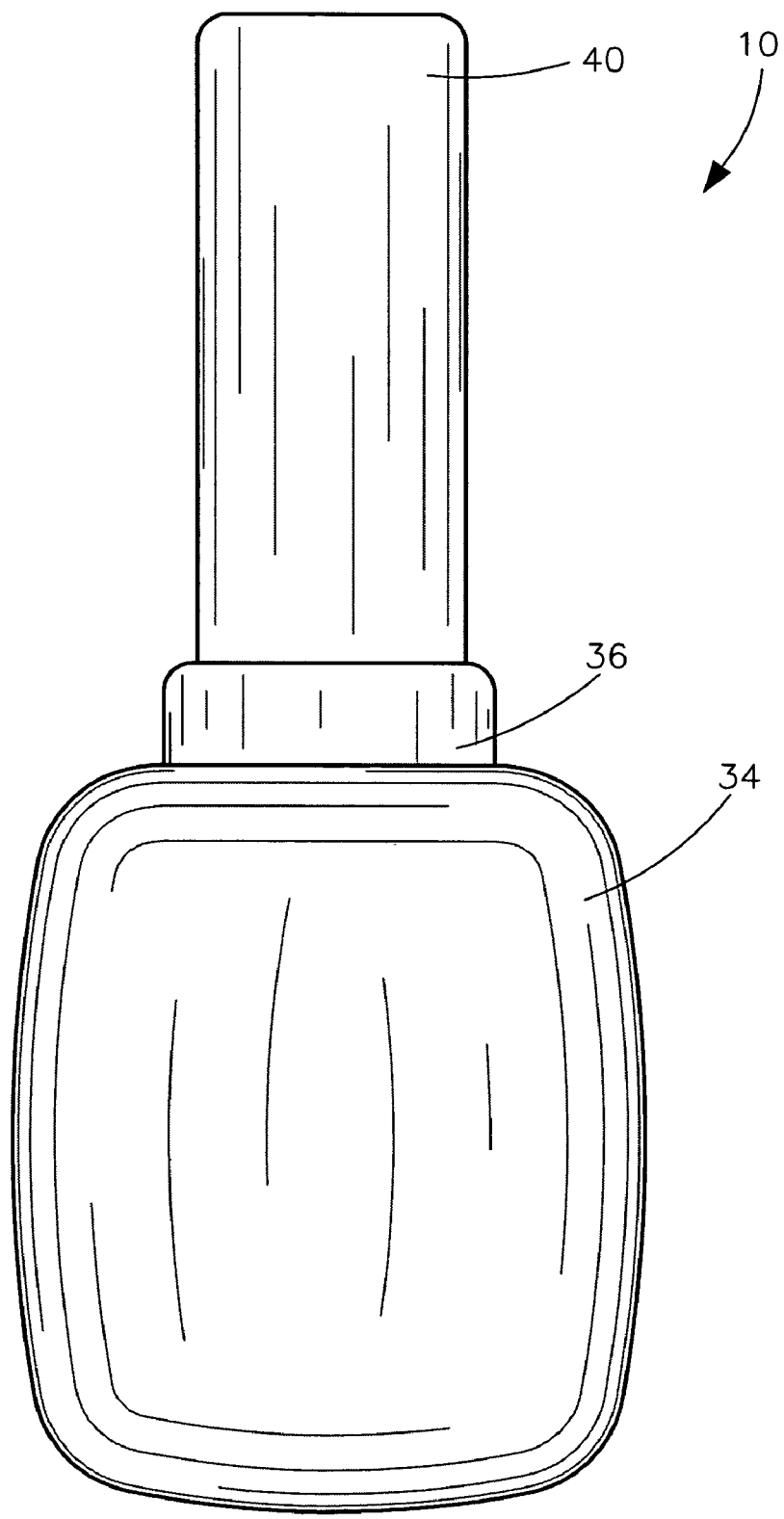
FIG. 2 is lateral elevation view of the apparatus shown in FIG. 1.

Referring to FIGS. 2 and 3, a smooth shouldered reinforcement member 36 is disposed atop each nose pad.

Referring again to FIG. 5, the U-shaped oblong tensing member 40 connects the first nose pad 20 to the second nose pad 30 at each reinforcement member 36. The memory wire 42 is disposed within the tensing member 40 in order to ensure adequate tension on a nose. The memory wire 42 is extended into each reinforcement member 36. While the apparatus 10 is provided in a variety of sizes, an overall height of about 1-1½ inches may be preferred by most users.

In an alternate embodiment 10', as shown in FIGS. 6-10b, each of the first and second nose pads 20', 30' are provided with a gel pack 50' that is removably mated directly to a corresponding one of the lateral pad sections 34', respectively. A smooth shouldered reinforcement member 36' is disposed atop each of the first and second nose pads 20', 30', respectively. A u-shaped oblong tensing member 40 preferably connects the first nose pad 20' to the second nose pad 20' at each of the reinforcement members 36'. Notably, the tensing member 40 is formed from deformably non-resilient material and thereby is adapted to conform to a contour of a user nose. A memory wire 42 may be disposed within the tensing member 40, wherein the memory wire 42 is further extended into each of the reinforcement members 36', respectively.

Each gel pack 50' may be provided with a rectangular depression 56' spaced inwardly from an outer border of the medial pad section 32' of each of the first and second nose pads 20', 30', respectively. Each of the first and second nose pads 20', 30' are independently displaced along a longitudinal length of the tensing member 40 such that opposed ends of the tensing member 40 become linearly reciprocated within the lateral pad sections 34' while each of the gel packs 50' remains statically mated to a corresponding one of the first and second nose pads 20', 30', as perhaps best shown in FIG. 6. In this manner, a user may selectively position the gel packs 50' to a desired location, as needed during extended use.

Figure 6:
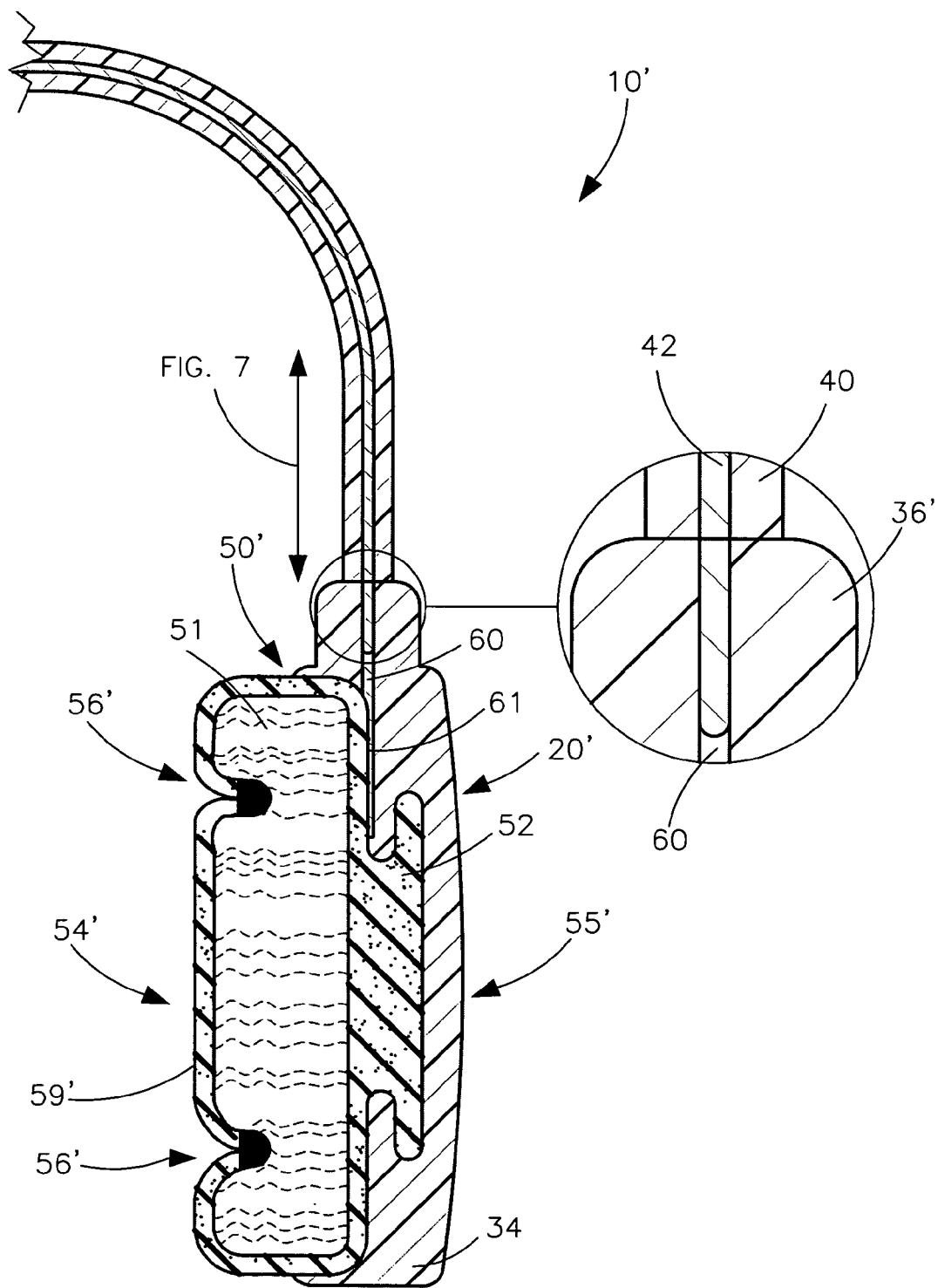
FIG. 6 is cross sectional showing the gel pack within the pad wherein the reinforcement member of the gel pack is slidably connected to the tension member such that the memory wire is adjustably interfitted within the pad, in accordance with an alternate embodiment of the present invention.
Figure 7:
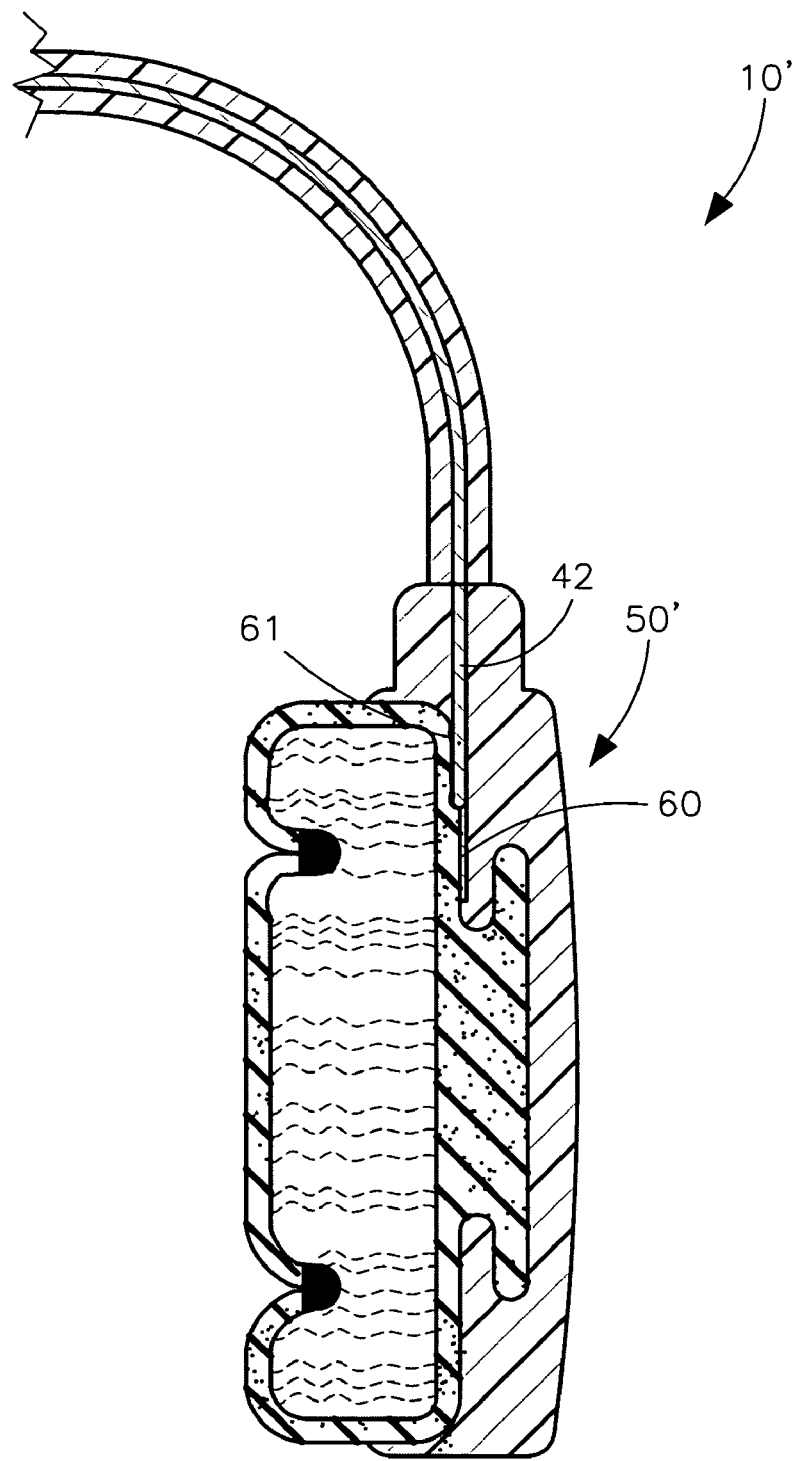
FIG. 7 is a cross-sectional view showing the gel pack displaced along the tension member such that the wire member is linear displaced downwardly into the pad.
Figure 8:
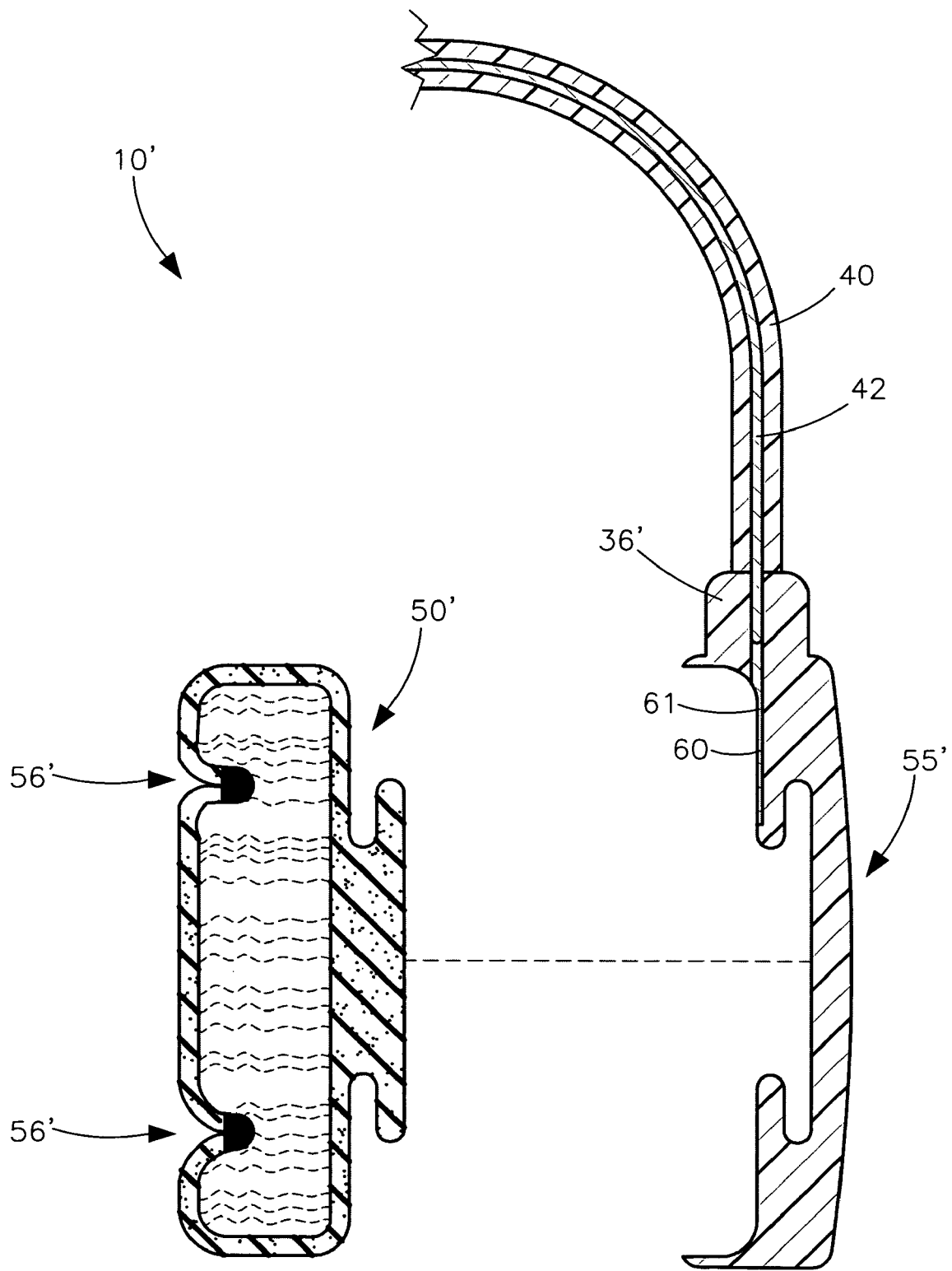
FIG. 8 is an exploded cross-sectional view showing the gel pack being removably mated to the pad.
Figure 9:
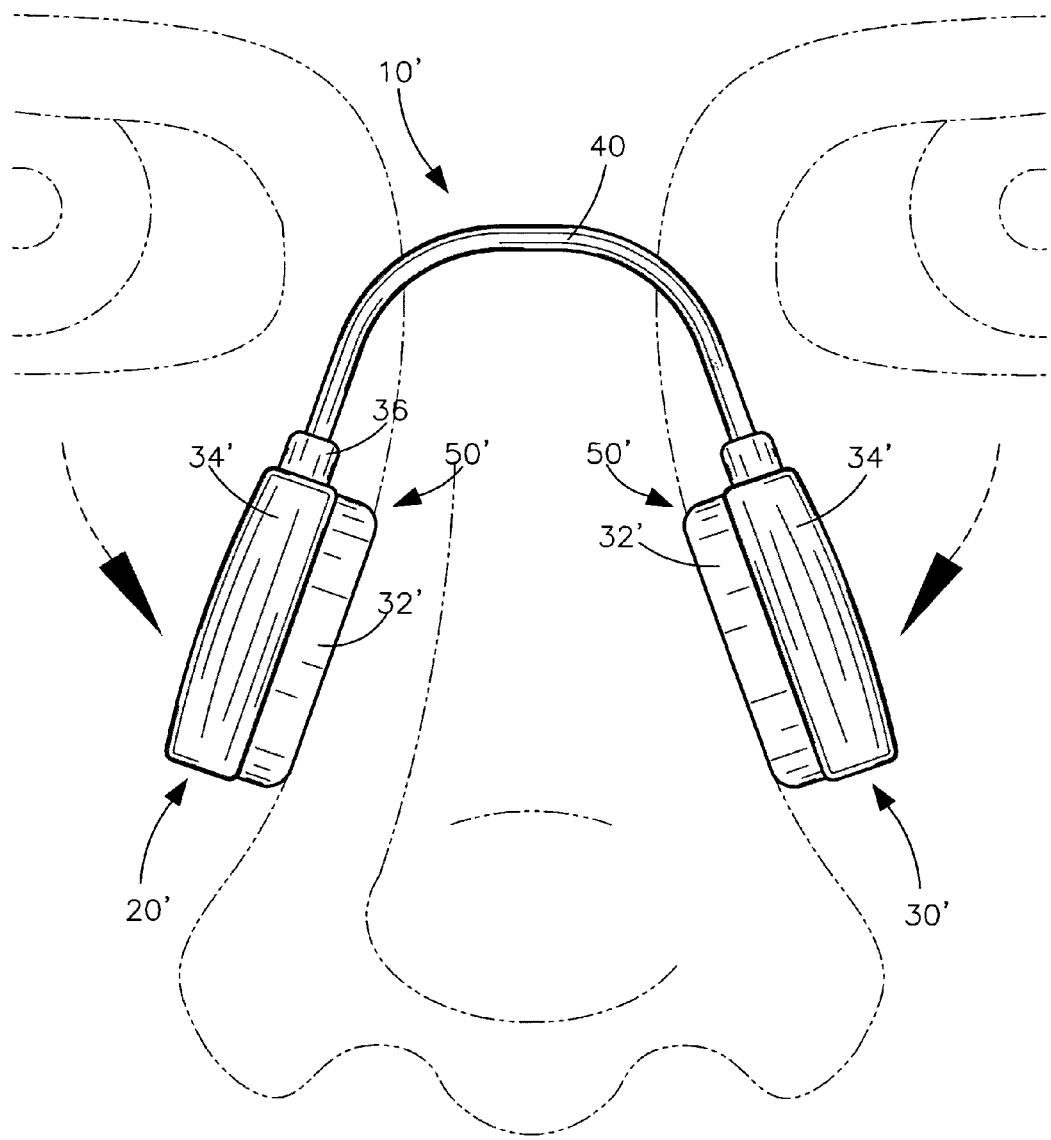
FIG. 9 is a front elevation view showing the nosebleed treatment apparatus positioned over a user's nostrils.

Referring to FIGS. 6 and 7, opposed ends of the tensing member 40 are magnetically coupled to a lateral face 61 of the gel packs respectively such that the first and second nose pads 20', 30' are prohibited from undesirably shifting along the longitudinal length of the tensing member 40 during operating conditions. For example, opposed ends of the memory wire 42 as well as the lateral faces 61 may be formed from magnetic material having opposite polarities to create an attracting force.

Figure 10B:
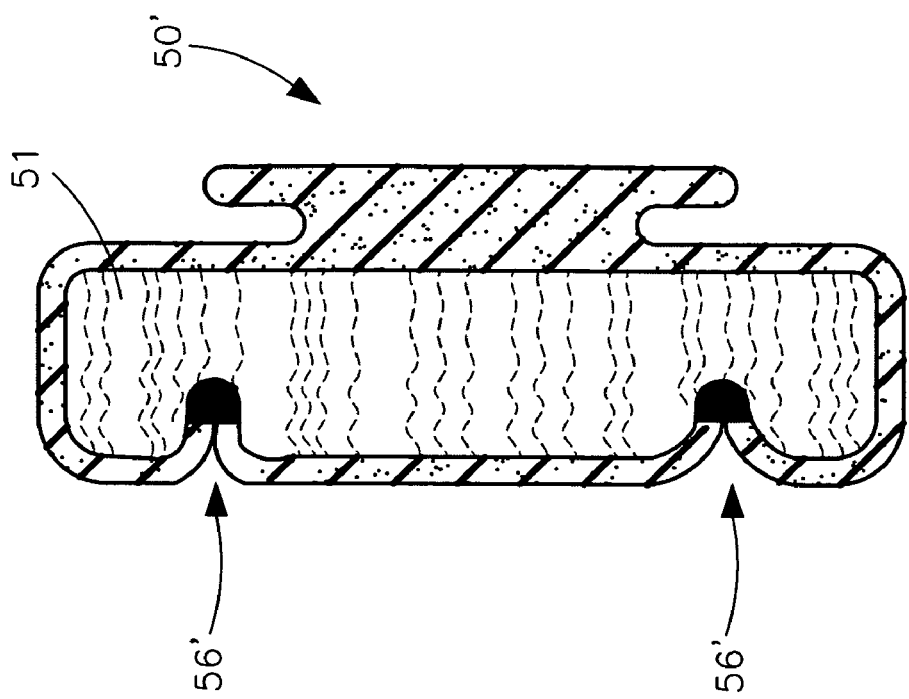
FIGS. 10a and 10b are cross-sectional views showing the depressions at substantially expanded and compressed positions when the gel pack is at thawed and frozen states, respectively.
Figure 10A:
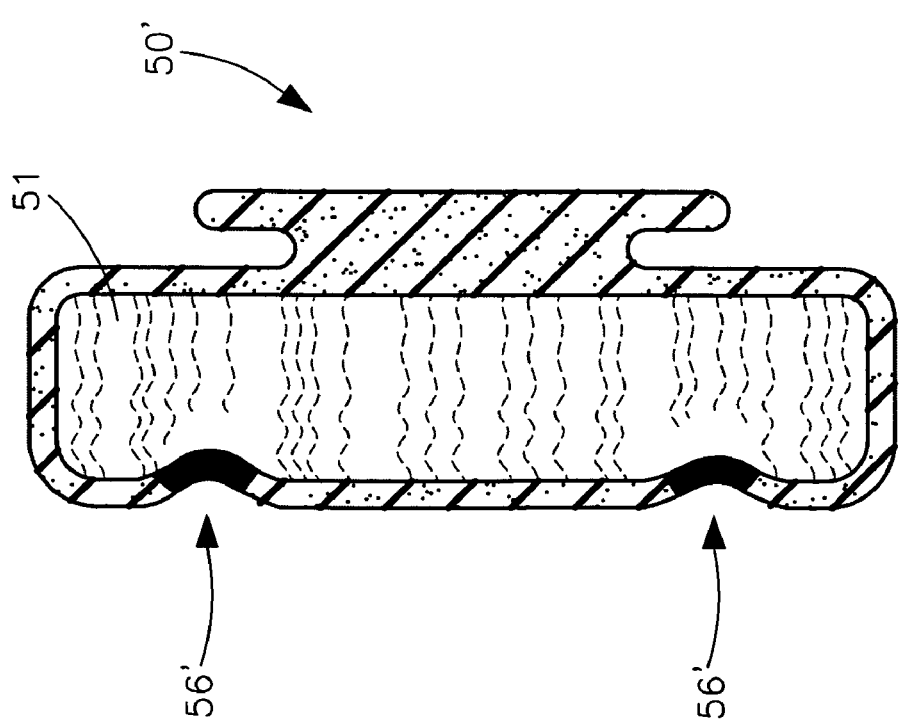

Now referring to FIGS. 10a, 10b, each of the depressions 56' preferably has a unique outer surface color (depicted by the shaded regions) that is distinct from a remaining outer surface color (depicted by the hatching pattern) of the gel packs 50' respectively. In particular, each of the depressions 6' has a dynamic shape and thereby morphs between first and second positions, shown in FIGS. 9b and 9a, respectively, when a corresponding one of the gel packs 50' is at a frozen state and a thawed state respectively. In other words, the depressions 56' are morphed when the gel packs 50 contract at the frozen state and expand at the thawed state, respectively. In this manner, the unique outer surface color (shaded region) is invisible and visible when the corresponding gel pack 50' is at the frozen state (FIG. 9*b*) and the thawed state (FIG. 9*a*), respectively, such that a user is able to quickly determine whether the corresponding gel pack 50' is at room temperature and below room temperature, respectively.

The present invention may further include a method for treating a nosebleed. Such a method preferably includes the chronological steps of: providing a pair of pliable mirror image nose pads including a first nose pad 20 and a second nose pad 30; providing and disposing a gel pack 50 within each the first and second nose pads 20, 30. Each gel pack 50 may have a first side spaced apart from a second side wherein the first side is adjacent to an inner surface of a medial pad section of each of the first and second nose pads 20, 30, and the second side is disposed within a lateral pad section of each the first and second nose pads 20, 30.

The present invention may further include the chronological steps of: providing and disposing a smooth shouldered reinforcement member 36 atop each of the first and second nose pads 20, 30, respectively; providing and connecting a U-shaped oblong tensing member 40 to the first and second nose pads 20, 30 at each of the reinforcement members 36 respectively wherein the tensing member 40 is formed from deformably non-resilient material; and firmly pressing the first and second nose pads 20, 30 against laterally opposed sides of the user nose by conforming the tensing member 40 to a contour of a user nose.

The combination of such claimed elements provides an unpredictable and unexpected result that is not rendered obvious by one skilled in the art. While designed as compactly as possible, the adjustability of the gel packs along with the morphing of the depressions provide the unexpected benefit of selectively repositioning the gel packs along the lateral walls of the user nose as well as quickly learning whether the gel packs should be re-chilled.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A nosebleed treatment apparatus, comprising:
   a pair of pliable mirror image nose pads comprising a first nose pad and a second nose pad;
   a gel pack disposed within each said first and second nose pads, each gel pack having a first side spaced apart from a second side, said first side being adjacent to an inner surface of a medial pad section of each said first and second nose pads, said second side being disposed within a lateral pad section of each said first and second nose pads;
   a smooth shouldered reinforcement member disposed adjacent each of said first and second nose pads respectively, along a longitudinal axis thereof; and
   a U-shaped oblong tensing member connecting said first nose pad to said second nose pad at each of said reinforcement members;
   a memory wire disposed within said tensing member.

2. The apparatus according to claim 1, further comprising: a rectangular depression spaced inwardly from an outer border of said medial pad section of each of said first and second nose pads respectively.

3. The apparatus according to claim 2, further comprising: a memory wire disposed within said tensing member.

4. The apparatus according to claim 3, wherein said memory wire is further extended into each said reinforcement member respectively.

5. The apparatus according to claim 4, wherein each of said first and second nose pads are independently displaced along a longitudinal length of said tensing member such that opposed ends of said tensing member become linearly reciprocated within said lateral pad sections while each of said gel packs remains statically mated to a corresponding one of said first and second nose pads respectively.

6. The apparatus according to claim 5, wherein each of said gel packs are removably mated directly to a corresponding one of said lateral pad sections respectively.

7. The apparatus according to claim 4, wherein said opposed ends of said tensing member are magnetically coupled to a lateral face of said gel packs respectively such that said first and second nose pads are prohibited from undesirably shifting along said longitudinal length of said tensing member during operating conditions.

8. The apparatus according to claim 7, wherein each of said depressions has a unique outer surface color that is distinct from a remaining outer surface color of said gel packs respectively;
   wherein each of said depressions has a dynamic shape and thereby morphs between first and second positions when a corresponding one of said gel packs is at a frozen state and a thawed state respectively;
   wherein said unique outer surface color is invisible and visible when said corresponding gel pack is at said frozen state and said thawed state respectively such that a user is able to quickly determine whether said corresponding gel pack is at a minimum temperature and a maximum temperature respectively.

9. A nosebleed treatment apparatus, comprising:
   a pair of pliable mirror image nose pads comprising a first nose pad and a second nose pad;
   a gel pack disposed within each said first and second nose pads, each gel pack having a first side spaced apart from a second side, said first side being adjacent to an inner surface of a medial pad section of each said first and second nose pads, said second side being disposed within a lateral pad section of each said first and second nose pads;
   a smooth shouldered reinforcement member disposed adjacent each of said first and second nose pads respectively, along a longitudinal axis thereof; and
   a U-shaped oblong tensing member connecting said first nose pad to said second nose pad at each of said reinforcement members;
   wherein said tensing member is formed from deformably non-resilient material and thereby is adapted to conform to a contour of a user nose;
   a memory wire disposed within said tensing member.

10. The apparatus according to claim 9, further comprising: a rectangular depression spaced inwardly from an outer border of said medial pad section of each of said first and second nose pads respectively.

11. The apparatus according to claim 10, further comprising: a memory wire disposed within said tensing member.

12. The apparatus according to claim 11, wherein said memory wire is further extended into each said reinforcement member respectively.

13. The apparatus according to claim 12, wherein each of said first and second nose pads are independently displaced along a longitudinal length of said tensing member such that opposed ends of said tensing member become linearly reciprocated within said lateral pad sections while each of said gel packs remains statically mated to a corresponding one of said first and second nose pads respectively.

14. The apparatus according to claim 13, wherein each of said gel packs are removably mated directly to a corresponding one of said lateral pad sections respectively.

15. The apparatus according to claim 12, wherein said opposed ends of said tensing member are magnetically coupled to a lateral face of said gel packs respectively such that said first and second nose pads are prohibited from undesirably shifting along said longitudinal length of said tensing member during operating conditions.

16. The apparatus according to claim 15, wherein each of said depressions has a unique outer surface color that is distinct from a remaining outer surface color of said gel packs respectively;

wherein each of said depressions has a dynamic shape and thereby morphs between first and second positions when a corresponding one of said gel packs is at a frozen state and a thawed state respectively;

wherein said unique outer surface color is invisible and visible when said corresponding gel pack is at said frozen state and said thawed state respectively such that a user is able to quickly determine whether said corresponding gel pack is at a minimum temperature and a maximum temperature respectively.

* * * * *